United States Patent
Vidal et al.

(10) Patent No.: US 6,551,360 B2
(45) Date of Patent: Apr. 22, 2003

(54) PYRAZOLINE-3,5-DIONE-CONTAINING COMPOSITIONS FOR DYEING KERATIN FIBRES; THEIR USE IN DYEING AS COUPLERS; DYEING PROCESS

(76) Inventors: Laurent Vidal, 7, rue do Rungis, F-75013, Paris (FR); Gérard Malle, 18 Grande Rue, F-77580, Villiers sur Morin (FR)

(*) Notice: Subject to any disclaimer, the term of this patent is extended or adjusted under 35 U.S.C. 154(b) by 0 days.

(21) Appl. No.: 09/750,166

(22) Filed: Dec. 29, 2000

(65) Prior Publication Data
US 2001/0054205 A1 Dec. 27, 2001

Related U.S. Application Data

(63) Continuation of application No. 09/155,192, filed as application No. PCT/FR97/00509 on Mar. 21, 1997.

(51) Int. Cl.$^7$ ................................................ A61K 7/13
(52) U.S. Cl. ........................ 8/405; 8/405; 8/406; 8/407; 8/408; 8/409; 548/366.4
(58) Field of Search ........................ 548/366, 366.4; 8/404, 405, 406, 407, 408, 409

(56) References Cited

U.S. PATENT DOCUMENTS

| | | | |
|---|---|---|---|
| 2,427,911 A | * 9/1947 | Kendall et al. | 548/366.4 |
| 2,439,098 A | 4/1948 | Porter et al. | 548/366.4 |
| 3,061,432 A | 10/1962 | Menzel et al. | 430/376 |
| 3,227,554 A | 1/1966 | Barr et al. | 430/382 |
| 3,379,533 A | * 4/1968 | Jenkins et al. | 548/366.4 |
| 3,419,391 A | 12/1968 | Young | 430/387 |
| 3,725,067 A | 4/1973 | Bailey et al. | 430/476 |
| 3,820,948 A | 6/1974 | Berth | 8/409 |
| 3,926,631 A | 12/1975 | Arai et al. | 430/226 |
| 4,128,425 A | * 12/1978 | Greenwald | 96/66 |
| 4,293,543 A | 10/1981 | Cotte et al. | 424/59 |
| 4,402,698 A | * 9/1983 | Kalopissis et al. | 8/405 |
| 4,500,630 A | 2/1985 | Sato et al. | 430/386 |
| 5,256,526 A | 10/1993 | Suzuki et al. | 430/384 |
| 5,441,863 A | 8/1995 | Tang et al. | |
| 5,457,210 A | 10/1995 | Kim et al. | 548/262.4 |
| 5,496,377 A | * 3/1996 | Samain et al. | 8/414 |
| 5,685,881 A | * 11/1997 | Rose et al. | 8/405 |
| 5,931,973 A | * 8/1999 | Malle et al. | 8/431 |
| 6,165,229 A | 12/2000 | Vidal et al. | 8/409 |
| 6,179,882 B1 | 1/2001 | Vidal et al. | 8/409 |

FOREIGN PATENT DOCUMENTS

| | | |
|---|---|---|
| DE | 2 160 317 | 6/1973 |
| DE | 2 359 999 | 6/1975 |
| DE | 3 731 395 | 4/1989 |
| DE | 3 843 892 | 6/1990 |
| DE | 4 009 097 | 9/1991 |
| DE | 4 133 957 | 4/1993 |
| EP | 0 030 680 | 6/1981 |
| EP | 0 119 860 | 9/1984 |
| EP | 0 285 274 | 10/1988 |
| EP | 0 304 001 | 2/1989 |
| EP | 0 309 652 | 4/1989 |
| EP | 0 320 764 | 6/1989 |
| EP | 0 456 226 | 11/1991 |
| EP | 0 488 248 | 6/1992 |
| EP | 0 488 909 | 6/1992 |
| EP | 0 518 238 | 12/1992 |
| EP | 0 547 864 | 6/1993 |
| EP | 0 557 851 | 9/1993 |
| EP | 0 578 248 | 1/1994 |
| EP | 0 591 103 | 4/1994 |
| FR | 1 564 999 | 4/1969 |
| FR | 2 075 583 | 10/1971 |
| FR | 2 466 492 | 4/1981 |
| FR | 2 586 913 | 3/1987 |
| GB | 1 026 978 | 3/1963 |
| GB | 1 153 196 | 6/1966 |
| GB | 1 458 377 | 9/1974 |
| JP | 58 42045 | 3/1983 |
| JP | 59 99437 | 6/1984 |
| JP | 59 162548 | 9/1984 |
| JP | 59 171956 | 9/1984 |
| JP | 60 33552 | 2/1985 |

(List continued on next page.)

OTHER PUBLICATIONS

English language translation of JP 7–84348, Konica Corp., pp. 1–35.
English language translation of JP 7–36,159, Konica Corp., pp. 1–50.

(List continued on next page.)

*Primary Examiner*—Yogendra N. Gupta
*Assistant Examiner*—Eisa Elhilo

(57) ABSTRACT

The present invention relates to a composition for dyeing keratin fibres, in particular human hair, containing, in a medium which is suitable for dyeing:

as coupler, at least one compound of formula:

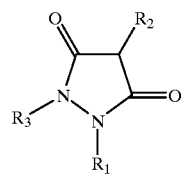

(I)

or one of the addition salts thereof with an acid, in which:

$R_2$ denotes, in particular, hydrogen, halogen, alkoxy, aryloxy, acetylamido, etc.

$R_1$ and $R_3$, which are independent, denote, in particular: hydrogen, alkyl, aryl, a heterocycle, etc.

it being understood that when $R_2$ and $R_1$ simultaneously represent a hydrogen atom, then $R_1$ is other than a hydrogen atom, a $C_1$–$C_5$ alkyl radical or a phenyl radical;

and at least one oxidation base.

34 Claims, No Drawings

FOREIGN PATENT DOCUMENTS

| | | | |
|---|---|---|---|
| JP | 60 43659 | | 3/1985 |
| JP | 60 172982 | | 9/1985 |
| JP | 60 190779 | | 9/1985 |
| JP | 62 79337 | | 12/1987 |
| JP | 63 169571 | | 7/1988 |
| JP | 62 36011 | | 8/1994 |
| JP | 7-36159 | * | 2/1995 |
| JP | 70 36159 | | 2/1995 |
| JP | 70 84348 | | 3/1995 |
| JP | 70 92632 | | 4/1995 |
| WO | WO 92/04349 | | 3/1992 |
| WO | WO 92/04883 | | 4/1992 |
| WO | WO 94/04130 | | 3/1994 |
| WO | WO 94/08959 | | 4/1994 |
| WO | WO 94/08969 | | 4/1994 |
| WO | WO 94/08970 | | 4/1994 |

OTHER PUBLICATIONS

H. Wilde et al., Synthese von 4H–Pyrazolo[1,5–a]benzimidazolen, Journal Für Praktische Chemie, pp. 829–836, 1984.

Co–pending U.S. application No. 09/142,951; Attorney Docket No.: 05725.0317–00000 Title: Keratin Fibre Dye Compositions Containing Pyrrolo–Azole Compounds, Use as Couplers, Dyeing Method Inventors: Laurent Vidal et al. U.S. Filing Date: Sep. 21, 1998.

Co–pending U.S. application No. (Not Yet Assigned); Attorney Docket No.: 05725–0317–01000 Title: Keratin Fibre Dye Compositions Containing Pyrrolo–Azole Compounds, Use as Couplers, Dyeing Method Preliminary Amendment filed Mar. 15, 2001 (copy enclosed) U.S. Filing Date: Mar. 15, 2001.

Co–pending U.S. application No. 09/666,046; Attorney Docket No.: 05725.0318–01000 Title: Imadazolo–Azole Containing Compositions for Dyeing Keratin Fibres; Their Use in Dyeing as Couplers, Dyeing Keratin Fibres; Their Use in Dyeing as Couplers, Dyeing Process Preliminary Amendment filed Sep. 20, 2000 (copy enclosed) Inventors: Laurent Vidal et al. U.S. Filing Date: Sep. 20, 2000.

Co–pending U.S. application No. 09/668,742; Attorney Docket No.: 05725.0319–01000 Title: Pyrazolo–Pyrimidineoxo Containing compositions for Dyeing Keratin Fibres; Their Use in Dyeing as Couplers, Dyeing Process Preliminary Amendment filed Sep. 25, 2000 (copy enclosed) Inventors: Laurent Vidal et al. U.S. Filing Date: Sep. 25, 2000.

Co–pending U.S. application No. 09/155,213; Attorney Docket No.: 05725–0328–00000 Title: Cosmetic Compositions Based on 4,5–Pyrazolinediones, Process for Their Preparation and Uses Thereof Inventors: Gérard Malle et al. U.S. Filing Date: Sep. 21, 1998.

* cited by examiner

PYRAZOLINE-3,5-DIONE-CONTAINING COMPOSITIONS FOR DYEING KERATIN FIBRES; THEIR USE IN DYEING AS COUPLERS; DYEING PROCESS

This is a continuation of application Ser. No. 09/155,192, filed Feb. 10, 1999, which is a national stage application under 35 U.S.C. § 371 of PCT/FR97/00509, filed Mar. 21, 1997, which is incorporated herein by reference.

The invention relates to a composition for the oxidation dyeing of keratin fibres, in particular human hair, containing at least one pyrazoline-3,5-dione compound as coupler and at least one oxidation base.

It is known to dye keratin fibres, and in particular human hair, with dye compositions containing oxidation dye precursors, in particular ortho- or para-phenylene diamines, ortho- or para-aminophenols, and heterocyclic compounds, which are generally referred to as oxidation bases. Oxidation dye precursors, or oxidation bases, are colorless or weakly coloured compounds which, when combined with oxidizing products, can give rise to colored compounds and dyes by a process of oxidative condensation.

It is known that the shades obtained with these oxidation bases can be varied by combining them with couplers or color modifiers, the latter being chosen in particular from aromatic meta-diamines, meta-aminophenols, meta-diphenols and certain heterocyclic compounds such as indole compounds.

The variety of molecules used as oxidation bases and couplers allows a wide range of colors to be obtained.

The so-called "permanent" coloration obtained by means of these oxidation dyes must moreover satisfy a certain number of requirements. Thus, it must have no toxicological drawbacks, it must allow shades to be obtained in the desired intensity and it must show good resistance to external agents (light, bad weather, washing, permanent-waving, perspiration, rubbing).

The dyes must also be able to cover grey hair and, lastly, they must be as unselective as possible, i.e. they must allow only the smallest possible colour differences to be obtained along the length of the same keratin fibre, which may, indeed, be differently sensitized (i.e. damaged) between its tip and its root.

The Applicant has now discovered that it is possible to obtain novel, powerful, unselective and particularly resistant dyes, which are capable of giving rise to intense colorations in varied shades, by using pyrazoline-3,5-dione compounds as couplers in the presence of an oxidation base.

This discovery forms the basis of the present invention.

The subject or the invention is a composition for dyeing keratin fibres, and in particular human keratin fibres such as the hair, characterized in that it comprises, in a medium which is suitable for dyeing:

as coupler, a least one pyrazoline-3,5-dione compound of formula (I), or one of the addition salts thereof with an acid;

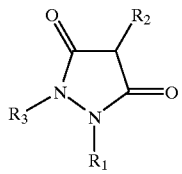

(I)

in which:

$R_2$ represents: a hydrogen atom; a halogen atom such as bromine, chlorine or fluorine; an acetylamido group; an alkoxy radical (such as, for example: methoxy, ethoxy, propyloxy, benzyloxy, methoxyethoxy, phenoxyethoxy, 2-cyanoethoxy, phenethyloxy, p-chlorobenzyloxy, methoxyethylcarbamoylmethoxy); an aryloxy radical (such as, for example: phenoxy, 4-methoxyphenoxy, 4-nitrophenoxy, 4-cyanophenoxy, 4-methanesulphonamidophenoxy, 4-methanesulphonylphenoxy, 3-methylphenoxy, 1-naphthyloxy); an acyloxy radical (such as, for example: acetoxy, propanoyloxy, benzoyloxy, 2,4-dichlorobenzoyloxy, ethoxyalkyloxy, pyruvyloyloxy, cinnamoyloxy, myristoyloxy); an arylthio radical (such as, for example: phenylthio, 4-carboxyphenylthio, 2-ethoxy-5-tert-butylphenylthio, 2-carboxyphenylthio, 4-methanesulphonylphenylthio); an alkylthio radical (such as, for example: methylthio, ethylthio, propylthio, butylthio, 2-cyanoethylthio, benzylthio, phenethylthio, 2-(diethylamino)ethylthio, ethoxyethylthio, phenoxyethylthio); a heteroarylthio radical (such as, for example: 5-phenyl-2,3,4,5-tetrazolylthio, 2-benzothiazolylthio); a heteroaryloxy radical (such as, for example: 5-phenyl-2,3,4,5-tetrazolyloxy, 2-benzothiazolyloxy); a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophnenylureido radical, an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1,2-dihydro-1-pyridyl radical; an alkylamido; an arylamido; a radical $NR^{III}R^{IV}$ with $R^{III}$ and $R^{IV}$, which may be identical or different, representing a $C_1$–$C_4$ alkyl, a hydoxyalkyl; a carboxyl; or an alkoxycarboxylic radical; $R_1$ and $R_3$ represent a hydrogen atom; a linear or branched $C_1$–$C_5$ alkyl radical; a $C_2$–$C_4$ mono- or polyhydroxyalkyl radical; a $C_2$–$C_4$ aminoalkyl radical; a phenyl radical; a phenyl radical substituted with a halogen atom or a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy or amino radical; or a radical

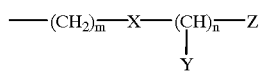

in which m and n are integers, which may be identical or different, between 1 and 3 inclusive, X represents an oxygen atom or an NH group, Y represents a hydrogen atom or a methyl radical, and Z represents a methyl radical, a group OR or NRR' in which R and R', which may be identical or different, denote a hydrogen atom, a methyl radical or an ethyl radical; an amino radical; a $C_1$–$C_4$ alkylamino; a carboxyl radical; an alkoxycarbonyl radical; an aryloxycarbonyl radical; a 5- or 6-membered heterocycle with at least one nitrogen, sulphur or oxygen atom (such as pyridyl, quinolyl, pyrrolyl, morpholyl, furyl, pyrazolyl, triazolyl, tetrazolyl, thiazolyl, oxazolyl, imadazolyl, thiadiazolyl); an acyl radical; a sulphonyl group; a phosphonyl group;

it being understood that when $R_2$ and $R_3$ simultaneously represent a hydrogen atom, then $R_1$ is other than a hydrogen atom, a $C_1$–$C_5$ alkyl radical or a phenyl radical;

and at least one oxidation base.

The addition salts with an acid for the compounds of the invention can be chosen in particular from hydrochlorides, hydrobromides, tartrates, tosylates, benzenesulphonates, sulphates, lactates and acetates.

Among the radicals $R_2$ of formula (I) defined above, the preferred radicals are chosen from the group consisting of:

a hydrogen atom; a $C_1$–$C_4$ alkoxy; phenoxy; phenoxy substituted with a halogen atom, a $C_1$–$C_4$ alkyl, a carboxyl, a trifluoromethyl group; an acyloxy radical; benzyloxy; $C_1$–$C_4$ alkylthio; phenylthio; phenylthio substituted with a halogen atom, a $C_1$–$C_4$ alkyl, a carboxyl, a trifluoromethyl group; a $C_1$–$C_4$ alkylamido; phenylamido; a radical $NR'''R^{IV}$ with $R'''$ and $R^{IV}$, which may be identical or different, representing a $C_1$–$C_4$ alkyl, a $C_1$–$C_4$ hydroxyalkyl; a carboxyl; a $C_1$–$C_4$ alkoxycarboxylic radical.

Among the radicals $R_2$ of formula (I) defined above, the radicals more particularly preferred are chosen from the group consisting of:

hydrogen; chlorine or bromine; methoxy or ethoxy; phenoxy; 4-methylhenoxy; acyloxy; benzyloxy; methylthio or ethylthio; phenylthio; 4-methylphenylthio, 2-tert-butylphenylthio; acetamido; phenylacetamido; dimethylamino; diethylamino; ethylmethylamino; (β-hydroxyethyl)methylamino.

Even more particularly, the preferred radicals $R_2$ are chosen from the group consisting of: hydrogen; chlorine; ethoxy; phenoxy; benzyloxy; acyloxy; acetamido; dimethylamino.

Among the radicals $R_1$ and $R_3$ of formula (I) defined above, the preferred radicals are chosen from the group consisting of: hydrogen; $C_1$–$C_4$ alkyl (such as methyl, ethyl, isopropyl, t-butyl, n-propyl); $C_2$–$C_4$ mono- or polyhydroxyalkyl (such as 2-hydroxyethyl, 3,4-dihydroxybutyl); $C_2$–$C_4$ aminoalkyl (such as 2-aminoethyl); dialkylaminoalkyl (such as 2-(N,N-dimethylamino)ethyl); phenyl; phenyl substituted with a chlorine atom, or a methoxy, nitro, trifluoromethyl, amino, methylamino or methyl radical; benzyl; benzyl substituted with a chlorine, a methoxy or a methyl; alkoxycarbonyl (such as methoxycarbonyl, ethoxycarbonyl); aryloxycarbonyl (such as phenyloxycarbonyl); pyridyl; furyl; thienyl; pyrrolyl; thiazolyl; acyl (such as acetyl, 2-ethylcarbonyl).

Among the radicals $R_1$ and $R_3$, the radicals more particularly preferred are chosen from the group consisting of:

hydrogen; methyl; ethyl; isopropyl, 2-hydroxyethyl; 2-aminoethyl; phenyl; 2-, 3- or 4-chlorophenyl; 3- or 4-methoxyphenyl; benzyl; 3- or 4-toluyl; methoxycarbonyl; ethoxycarbonyl; pyridyl; pyrazolyl; pyrrolyl.

Even more particularly, the preferred radicals $R_1$ and $R_3$ are chosen from the group consisting of:

hydrogen; methyl; ethyl; isopropyl; phenyl; 4-chlorophenyl; 4-toluyl; benzyl; pyridyl; pyrazolyl.

The compounds of formula (I) more particularly preferred are those for which:
$R_1$ denotes hydrogen, methyl, ethyl or phenyl;
$R_2$ denotes chlorine or ethoxy;
$R_3$ denotes methyl, ethyl or phenyl.

As compounds of formula (I) above, mention may be made most particularly of:

1,2-diphenylpyrazoline-3,5-dione,
1,2-diethylpyrazoline-3,5-dione,
1,2-dimethylpyrazoline-3,5-dione,
4-chloro-1,2-diethylpyrazoline-3,5-dione,
and the addition salts thereof with an acid.

The pyrazoline-3,5-dione compounds of the invention, their synthetic intermediates and processes for their preparation are described in the patents and patent applications JP 07-036,159, JP 07-084,348 and U.S. Pat. No. 4,128,425, and in the following publications:

L. Wyzgowska, Acta. Pol. Pharm. 1982, 39 (1–3), 83.
E. Hannig, Pharmazie, 1980, 35 (4), 231
M. H. Elnagdi, Bull. Chem. Soc Jap., 46 (6), 1830, 1973
G. Cardillo, Gazz. Chim. Ital. 1966, 95, (8–9), 973.

The compound(s) of formula (I) preferably represent(s) from 0.0005 to 12% by weight approximately relative to the total weight of the dye composition, and even more preferably from 0.005 to 6% by weight approximately relative to this weight.

The nature of the oxidation base(s) which can be used in the dye composition according to the invention is not critical. This or these oxidation bases is(are) preferably chosen from para-phenylenediamines, bis(phenyl) alkylenediamines, para-aminophenols, ortho-aminophenols and heterocyclic bases, and the addition salts thereof with an acid.

Among the para-phenylenediamines which can be used as oxidation bases in the dye composition according to the invention, mention may be made in particular of the compounds corresponding to formula (II) below, and the addition salts thereof with an acid:

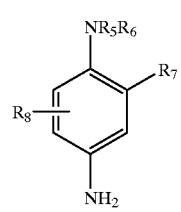

(II)

in which:

$R_5$ represents a hydrogen a $C_1$–$C_4$ alkyl, $C_1$–$C_4$ monohydroxyakyl, $C_2$–$C_4$ polyhydroxyalkyl or ($C_1$–$C_4$) alkoxy($C_1$–$C_4$)alkyl radical, $R_6$ represents a hydrogen atom or a $C_1$–$C_4$ alkyl, $C_1$–$C_4$ monohydroxyalkyl or $C_2$–$C_4$ polyhydroxyalkyl radical, $R_7$ represents a hydrogen atom, a halogen atom such as a chlorine atom, or a $C_1$–$C_4$ alkyl, sulpho, carboxyl, $C_1$–$C_4$ monohydroxyalkyl or $C_1$–$C_4$ hydroxyalkoxy radical, $R_8$ represents a hydrogen atom or a $C_1$–$C_4$ alkyl radical.

In formula (II) above, and when $R_7$ is other than a hydrogen atom, then $R_5$ and $R_6$ preferably represent a hydrogen atom and $R_7$ is preferably identical to $R_8$, and when $R_7$ represents a halogen atom, then $R_5$, $R_6$ and $R_8$ preferably represent a hydrogen atom.

Among the para-phenylenediamines of formula (II) above, mention may be made more particularly of paraphenylenediamine, para-toluylenediamine, 2-isopropyl-para-phenylenediamine, 2-β-hydroxyethyl-para-phenylenediamine, 2-β-hydroxyethyloxy-paraphenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-(β-methoxyethyl) aminobenzene and 2-chloro-para-phenylenediamine, and the addition salts thereof with an acid.

Among the bis(phenyl)alkylenediamines which can be used as oxidation bases in the dye composition according to the invention, mention may be made in particular of the compounds corresponding to formula (III) below, and the addition salts thereof with an acid:

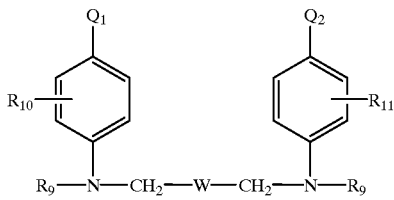

(III)

in which:

$Q_1$ and $Q_2$, which may be identical or different, represent a hydroxyl radical or a radical $NHR_{12}$ in which $R_{12}$ represents a hydrogen atom or a $C_1$–$C_4$ alkyl radical, $R_9$ represents a hydrogen atom or a $C_1$–$C_4$ alkyl, $C_1$–$C_4$ monohydroxyalkyl, $C_2$–$C_4$ polyhydroxyalkyl or $C_1$–$C_4$ aminoalkyl radical in which the amino residue may be substituted, $R_{10}$ and $R_{11}$, which may be identical or different, represent a hydrogen or halogen atom or a $C_1$–$C_4$ alkyl radical, W represents a radical taken from the group consisting of the following radicals —(CH$_2$)$_n$—; —(CH$_2$)$_m$—O—(CH$_2$)$_m$; —(CH$_2$)$_m$—CHOH—(CH$_2$)$_m$ and 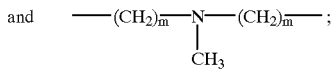

in which n is an integer between 0 and 8 inclusive and m is an integer between 0 and 4 inclusive Among the bis(phenyl)alkylenediamines of formula (III) above, mention may be made more particularly of N,N'-bis(β-hydroxyethyl-N,N'-bis-(4'-aminophenyl)-1,3-diamino-2-propanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the addition salts thereof with an acid.

Among these bis(phenyl)alkylenediamines of formula (III), N,N'-bis(β-hydroxyethyl)-N,N'-bis(4'-aminophenyl)-1,3-diaminopropanol or one of the addition salts thereof with an acid is particularly preferred.

Among the para-aminophenols which can be used as oxidation bases in the dye composition according to the invention, mention may be made in particular of the compounds corresponding to formula (IV) below, and the addition salts thereof with an acid:

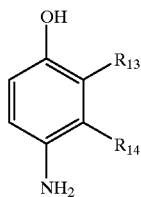

(IV)

in which:

$R_{13}$ represents a hydrogen atom or a $C_1$–$C_4$ alkyl, $C_1$–$C_4$ monohydroxyalkyl, ($C_1$–$C_4$)alkoxy($C_1$–$C_4$)alkyl or $C_1$–$C_4$ aminoalkyl radical, $R_{14}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, cyano($C_1$–$C_4$)alkyl or ($C_1$–$C_4$)alkoxy ($C_1$–$C_4$)alkyl radical, it being understood that at least one of the radicals $R_{13}$ or $R_{14}$ represents a hydrogen atom.

Among the para-aminophenols of formula (IV) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

Among the ortho-aminophenols which can be used as oxidation bases in the dye composition according to the invention, mention may be made in particular of 2-aminophenol, 2-amino-1-hydroxy-5-methylbenzere, 2-amino-1-hydroxy-6-methylbenzene and 5-acetamido-2-aminophenol, and the addition salts thereof with an acid.

Among the heterocyclic bases which can be used as oxidation bases in the dye composition according to the invention, mention may be made in particular of pyridine derivatives, pyrimidine derivatives and pyrazole derivatives and the addition salts thereof with an acid.

Among the pyridine derivatives, mention may be made more particularly of the compounds described, for example, in GB patents 1,026,978 and 1,153,196, such as 2,5-diaminopyridine, and the addition salts thereof with an acid.

Among the pyrimidine derivatives, mention may be made more particularly of compounds described, for example, in German patent DE 2,359,399 or Japanese patents JP 88-169,571 and JP 91-333,495, such as 2,4,5,6-tetraaminopyrimidine and 4-hydroxy-2,5,6-triaminopyrimidine, and the addition salts thereof with an acid.

Among the pyrazole derivatives, mention may be made more particularly of the compounds described in patents DE 3,843,892 and DE 4,133,957 and patent applications WO 94/08969 and WO 94/08970, such as 4, 5-diamino-1-methylpyrazole and 3,4-diaminopyrazole, and 1-(4'-chlorobenzyl)-4,5-diaminopyrazole, and the addition salts thereof with an acid.

According to the invention, the oxidation base(s) preferably represent(s) from 0.0005 to 12% by weight approximately relative to the total weight of the dye composition, and even more preferably from 0.005 to 6%. by weight approximately relative to this weight.

The dye composition according to the invention can also contain one or more additional couplers other than the compounds of formula (I) and/or one or more direct dyes, so as to vary the shades obtained with the oxidation bases or to enrich the shades with glints.

The additional couplers which can be used in the composition according to the invention can be chosen from the couplers used conventionally in oxidation dyeing, and among which mention may be made in particular of meta-phenylenediamines, meta-aminophenols, meta-diphenols and heterocyclic couplers such as, for example, indole derivatives, indoline derivatives, and the addition salts thereof with an acid.

These couplers can be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis (2,4-diaminophenoxy)propane, sesamol, α-naphthol, 6-hydroxyindole, 4-hydroxyindole, 4-hydroxy-N-methylindole and 6-hydroxyindoline, and the addition salts thereof with an acid.

When they are present, these additional couplers preferably represent from 0.0005 to 5% by weight approximately relative to the total weight of the dye composition, and even more preferably from 0.005 to 3% by weight approximately relative to this weight The addition salts with an acid for he oxidation base(s) and/or for the additional couplers which can be used in the dye composition of the invention are chosen in particular from the hydrochlorides, hydrobromides, sulphates, tartrates, lactates and acetates.

The medium which is suitable for dyeing (or the support) generally consists of water or of a mixture of water and at least one organic solvent for dissolving the compounds which would not be sufficiently water-soluble. As organic solvents, mention may be mad, for example, of $C_1$–$C_4$ lower alcohols, such as ethanol and isopropanol; glycerol; glycols and glycol ethers such as 2-butoxyethanol, propylene glycol, propylene glycol monomethyl ether, diethylene glycol monoethyl ether and monomechyl ether, and aromatic alcohols such as benzyl alcohol or phenoxyethanol, similar products and mixtures thereof.

The solvents can be present in proportions preferably of between 1% and 40% by weight approximately relative to the total weight of the dye composition, and even more preferably between 5 and 30% by weight approximately.

The pH of the dye composition in accordance with the invention is generally between 3 and 12. it can be adjusted to the desired value using acidifying or basifyving agents usually used co dye keratin fibres.

Among the acidifying agents, mention may be made, by way of example, of inorganic or organic acids such as hydrochloric acid, orthophosphoric acid, carboxylic acids such as tartaric acid, citric acid and lactic acid, and sulphonic acids.

Among the basifying agents, mention may be made, by way of example, of aqueous ammonia, alkaline carbonates, alkanolamines such as mono-, di- and triethanolamines and derivatives thereof, sodium hydroxide, potassium hydroxide and the compounds of formula (V) below:

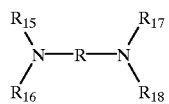

(V)

in which R is a propylene residue optionally substituted with a hydroxyl group or a $C_1$–$C_4$ alkyl radical; $R_{15}$, $R_{16}$, $R_{17}$ and $R_{18}$, which may be identical or different, represent a hydrogen atom or a $C_1$–$C_4$ alkyl or $C_1$–$C_4$ hydroxyalkyl radical.

The dye composition according to the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifiers.

Needless to say, the person skilled in the art will take care to select the optional complementary compound(s) mentioned above, such that the advantageous properties intrinsically associated with the dye composition according to the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The subject of the invention is also the use of the pyrazoline-3,5-diones of formula (I) above, as couplers, in combination with at least one oxidation base for the oxidation dyeing of keratin fibres, and in particular human keratin fibres such as the hair.

Another subject of the invention is a process for the oxidation dyeing of keratin fibres, and in particular human keratin fibres such as the hair, using the dye composition as defined above.

According to this process, at least one dye composition as defined above is applied to the fibres, the color being developed at acidic, neutral or alkaline pH using an oxidizing agent which is added to the dye composition only at the moment of use, or which is present in an oxidizing composition that is applied simultaneously or sequentially in a separate manner.

According to a particularly preferred embodiment of the dyeing process according to the invention, the dye composition described above is mixed, at the moment of use, with an oxidizing composition containing, in a medium which is suitable for dyeing, at least one oxidizing agent that is present in an amount which is sufficient to develop a coloration. The mixture obtained is then applied to the keratin fibres and is left to stand on them for 3 to 50 minutes approximately, preferably 5 to 30 minutes approximately, after which the fibres are rinsed, washed with shampoo, rinsed again and dried.

The oxidizing agent present in the oxidizing composition as defined above can be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that after mixing with the dye composition, the pH of the resulting composition applied to the keratin fibres preferably ranges between 3 and 12 approximately and even more preferably between 5 and 11. It is adjusted to the desired value using acidifying or basifying agents usually used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams or gels or in any other form which is suitable for dyeing keratin fibres, and in particular human hair.

Another subject of the invention is a dyeing "kit" or multi-compartment device or any other multi-compartment packaging system in which a first compartment contains one dye composition as defined above and a second compartment contains the oxidizing composition as defined above.

These devices can be equipped with means which allow the desired mixture to be delivered onto the hair, such as the devices described in patent FR-2,586,913 in the name of the Applicant.

EXAMPLES

Examples 1 and 2 of Dyeing in Alkaline Medium

The following dye compositions, in accordance with the invention, were prepared (contents in grams):

| EXAMPLE | 1 | 2 |
|---|---|---|
| 1,2-Diphenylpyrazoline-3,5-dione (coupler) | 0.756 | — |
| 1,2-Diethylpyrazoline-3,5-dione (coupler) | — | 0.468 |
| Para-phenylenediamine | 0.324 | — |
| 1,3-Dimethyl-4,5-diaminoyrazole dihydrochloride (oxidation base) | — | 0.597 |
| Common dye support | (*) | (*) |
| Demineralized water qs | 100 g | 100 g |

NB: the 1,2-diphenylpyrazoline-3,5-dione and the 1,2-diethylpyrazoline-3,5-dione were prepared according to the synthetic process described in U.S. Pat. No. 4,128,425.

| (*) Common dye support: | |
|---|---|
| Benzyl alcohol | 2.0 g |
| Polyethylene glycol containing 6 mol of ethylene oxide | 3.0 g |
| Ethanol | 20.0 g |
| ($C_8$–$C_{12}$) Alkylpolyglucoside as an aqueous solution containing 60% active material, buffered with ammonium citrate, sold under the name Oramix CG110 by the company SEPPIC | 6.0 g |
| Aqueous ammonia containing 20% $NH_3$ | 10.0 g |
| Sodium metabisulphite | 0.228 g |
| Sequestering agent    qs | |

At the moment of use, each dye composition was mixed with an equal weight-amount of an aqueous ammonium persulphate solution at a concentration of $6 \times 10^{-3}$ mol %.

The mixture obtained was applied for 30 minutes to locks of permanent-waved or non-permanent-waved natural grey hair containing 90% white hairs, at a rate of 10 g per 1 g of hair. After rinsing, washing with a standard shampoo and drying, the locks were dyed in the shades featured in the table below:

| Example | pH of the mixture | Shade obtained on natural grey hair containing 90% white hairs | Shade obtained on permanent-waved grey hair containing 90% white hairs |
|---|---|---|---|
| 1 | 9.3 | deep, "washed" iridescent | deep, "washed" iridescent |
| 2 | 9.9 | light saffron-yellow | saffron-yellow |

What is claimed is:
1. A composition for dyeing keratin fibers comprising:
(a) at least one coupler chosen from at least one pyrazoline-3,5-dione compound of formula (I) and acid addition salts thereof:

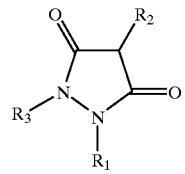

(I)

wherein:
$R_2$ is chosen from a hydrogen atom; a halogen atom; an acetylamido radical; an alkoxy radical; an acyloxy radical; an aryloxy radical; an arylthio radical; an alkylthio radical; a heteroarylthio radical; a heteroaryloxy radical; a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical, an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1,2-dihydro-1-pyridyl radical; an alkylamido radical; an arylamido radical; a radical $NR'''R^{IV}$, wherein $R'''$ and $R^{IV}$, which may be identical or different, are each chosen from a $C_1$–$C_4$ alkyl radical, a hydroxyalkyl radical; a carboxyl radical; and an alkoxycarboxyl radical; wherein all of said radicals are substituted or unsubstituted;

$R_1$ and $R_3$, which may be identical or different, are each chosen from a hydrogen atom; a $C_1$–$C_5$ alkyl radical; a $C_2$–$C_4$ mono- or polyhydroxyalkyl radical; a $C_2$–$C_4$ aminoalkyl radical; a phenyl radical; a phenyl radical substituted with a halogen atom or a $C_1$–$C_4$ alkyl radical, a $C_1$–$C_4$ alkoxy radical, a nitro radical, a trifluoromethyl radical, an amino radical, or a $C_1$–$C_4$ alkylamino radical; a benzyl radical; a benzyl radical substituted with a halogen atom, a $C_1$–$C_4$ alkyl radical, a $C_1$–$C_4$ alkoxy radical, a methylenedioxy radical, or amino radical; and a radical

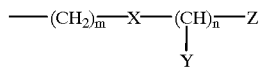

wherein m and n, which may be identical or different, are each chosen from integers ranging from 1 to 3, X is chosen from an oxygen atom and an NH group, Y is chosen from a hydrogen atom and a methyl radical, and Z is chosen from a methyl radical; a group OR or NRR', wherein R and R', which may be identical or different, are each chosen from a hydrogen atom, a methyl radical and an ethyl radical; an amino radical; a $C_1$–$C_4$ alkylamino radical; a carboxyl radical; an alkoxycarbonyl radical; an aryloxycarbonyl radical; a 5- or 6-membered heterocycle with at least one nitrogen, sulphur or oxygen atom; an acyl radical; a sulphonyl group; and a phosphonyl group;

wherein when $R_2$ and $R_3$ simultaneously represent a hydrogen atom, then $R_1$ is other than a hydrogen atom, a $C_1$–$C_5$ alkyl radical or a phenyl radical; and (b) at least one oxidation base chosen from para-phenylenediamines bis(phenyl)alkylenediamines para-aminophenols, ortho-aminophenols, heterocyclic bases, and acid addition salts thereof, wherein said para-phenylenediamines are chosen from compounds of formula (II):

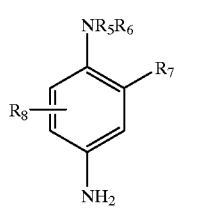

(II)

wherein:

$R_5$ is chosen from a hydrogen atom, a $C_1$–$C_4$ alkyl radical, a $C_1$–$C_4$ monohydroxyalkyl radical, a $C_2$–$C_4$ polyhydroxyalkyl radical and a ($C_1$–$C_4$)alkoxy($C_1$–$C_4$)alkyl radical, $R_6$ is chosen from a hydrogen atom, a $C_1$–$C_4$ alkyl radical, a $C_1$–$C_4$ monohydroxyalkyl radical and a $C_2$–$C_4$ polyhydroxyalkyl radical, $R_7$ is chosen from a hydrogen atom, a halogen atom, a $C_1$–$C_4$ alkyl radical, a sulpha radical, a carboxyl radical, a $C_1$–$C_4$ monohydroxyalkyl radical and a $C_1$–$C_4$ hydroxyalkoxy radical, and $R_8$ is chosen from a hydrogen atom and a $C_1$–$C_4$ alkyl radical, wherein when one of $R_5$ and $R_6$ is ethyl, the other one of $R_5$ and $R_6$ is not hydroxyethyl, and further wherein said at least one coupler and said at least one oxidation base are present in said composition in an amount effective for dyeing keratin fibers, and (c) a medium suitable for dyeing keratin fibers.

2. A composition according to claim 1, wherein said keratin fibers are human keratin fibers.

3. A composition according to claim 2, wherein said human keratin fibers are hair.

4. A composition according to claim 1, wherein for $R_2$, said halogen atom is chosen from bromine, chlorine and fluorine; said alkoxy radical is chosen from methoxy, ethoxy, propyloxy, benzyloxy, methoxyethoxy, phenoxyethoxy, 2-cyanoethoxy, phenethyloxy, p-chlorobenzyloxy, and methoxyethylcarbamoylmethoxy; said acyloxy radical is chosen from acetoxy, propanoyloxy, benzoyloxy, 2,4-dichlorobenzoyloxy, ethoxyalkyloxy, pyruvyloyloxy, cinnamoyloxy, and myristoyloxy; said arylthio radical is chosen from phenylthio, 4-carboxyphenylthio, 2-ethoxy-5-tert-butylphenylthio, 2-carboxyphenylthio, and 4-methanesulphonylphenylthio; said akylthio radical is chosen from methylthio, ethylthio, propylthio, butylthio, 2-cyanoethylthio, benzylthio, phenethylthio, 2-(diethylamino)ethylthio, ethoxyethylthio, and phenoxyethylthio; said heteroarylthio radical is chosen from 5-phenyl-2,3,4,5-tetrazolylthio, and 2-benzothiazolylthio; and said heteroaryloxy radical is chosen from 5-phenyl-2,3,4,5-tetrazolyloxy, and 2-benzothiazolyloxy.

5. A composition according to claim 1, wherein said $R_1$ and $R_3$, which may be identical or different, are each chosen from: hydrogen; a $C_1$–$C_4$ alkyl radical; a $C_2$–$C_4$ mono- and polyhydroxyalkyl radical; a $C_2$–$C_4$ aminoalkyl radical; a phenyl radical; a dialkylaminoalkyl radical; a phenyl radical substituted with a radical chosen from chlorine, methoxy, nitro, trifluoromethyl, amino, methylamino and methyl; a benzyl radical; a benzyl radical substituted with a radical chosen from chlorine, methoxy and methyl; an alkoxycarbonyl radical; an aryloxycarbonyl radical; a pyridyl radical; a furyl radical; a thienyl radical; a pyrrolyl radical; a thiazolyl radical; and an acyl radical.

6. A composition according to claim 5, wherein said radicals $R_1$ and $R_3$, which may be identical or different, are each chosen from: hydrogen; methyl; ethyl; isopropyl; 2-hydroxyethyl; 2-aminoethyl; phenyl; 2-chlorophenyl; 3-chlorophenyl; 4-chlorophenyl; 3-methoxyphenyl; 4-methoxyphenyl; 3-toluyl; 4-toluyl; benzyl; methoxycarbonyl; ethoxycarbonyl; pyridyl; pyrazolyl; and pyrrolyl.

7. A composition according to claim 6, wherein said radicals $R_1$ and $R_3$, which may be identical or different, are each chosen from: hydrogen; methyl; ethyl; isopropyl; phenyl; 4-chlorophenyl; 4-toluyl; benzyl; pyridyl; and pyrazolyl.

8. A composition according to claim 1, wherein for $R_1$, said 5- or 6-membered heterocycle is chosen from pyridyl, quinolyl, pyrrolyl, morpholyl, furyl, pyrazolyl, triazolyl, tetrazolyl, thiazolyl, oxazolyl, imidazolyol, and thiadiazolyl.

9. A composition according to claim 1, wherein said acid addition salts are chosen from hydrochlorides, hydrobromides, tartrates, tosylates, benzenesulphonates, sulphates, lactates and acetates.

10. A composition according to claim 1, wherein said radicals $R_2$ are chosen from: a hydrogen atom; a $C_1$–$C_4$ alkoxy radical; a phenoxy radical; a phenoxy radical substituted with a radical chosen from halogen, $C_1$–$C_4$ alkyl, carboxyl, and trifluoromethyl; an acyloxy radical; a benzyloxy radical; a $C_1$–$C_4$ alkylthio radical; a phenylthio radical; a phenylthio radical substituted with a radical chosen from halogen, $C_1$–$C_4$ alkyl, carboxyl, and trifluoromethyl; a $C_1$–$C_4$ alkylamido radical; a phenylamido radical; a radical $NR^{III}R^{IV}$, wherein $R^{III}$ and $R^{IV}$, which may be identical or different, are each chosen from a $C_1$–$C_4$ alkyl radical; a $C_1$–$C_4$ hydroxyalkyl radical; a carboxyl radical; and a $C_1$–$C_4$ alkoxycarboxyl radical.

11. A composition according to claim 10, wherein said radicals $R_2$ are chosen from: hydrogen; chlorine; bromine; methoxy; ethoxy; phenoxy; 4-methylphenoxy; acyloxy; benzyloxy; methylthio; ethylthio; phenylthio; 4-methylphenylthio; 2-tert-butylphenylthio; acetamido; phenylacetamido; dimethylamino; diethylamino; ethylmethylamino; and (β-hydroxyethyl)methylamino.

12. A composition according to claim 1, wherein said radicals $R_2$ are chosen from: hydrogen; chlorine; ethoxy; phenoxy; benzyloxy; acyloxy; acetamido; and dimethylamino.

13. A composition according to claim 1, wherein for said at least one pyrazoline-3,5-dione compound of formula (I)

R₁ is chosen from hydrogen, methyl, ethyl and phenyl; R₂ is chosen from chlorine and ethoxy; and R₃ is chosen from methyl, ethyl and phenyl.

14. A composition according to claim 1, wherein said at least one pyrazoline-3,5-dione compound of formula (I) is chosen from:
   1,2-diphenylpyrazoline-3,5-dione,
   1,2-diethylpyrazoline-3,5-dione,
   1,2-dimethylpyrazoline-3,5-dione,
   4-chloro-1,2-diethylpyrazoline-3,5-dione,
and acid addition salts thereof.

15. A composition according to claim 15, wherein said at least one pyrazoline-3,5-dione compound of formula (I) is present in an amount ranging from 0.0005 to 12% by weight relative to the total weight of said composition.

16. A composition according to claim 15, wherein said at least one pyrazoline-3,5-dione compound of formula (I) is present in an amount ranging from 0.005 to 6% by weight relative to the total weight of said composition.

17. A composition according to claim 1, wherein said at least one oxidation base is present in an amount ranging from 0.0005 to 12% by weight relative to the total weight of said composition.

18. A composition according to claim 17, wherein said at least one oxidation base is present in an amount ranging from 0.005 to 6% by weight relative to the total weight of said composition.

19. A composition according to claim 1, wherein said composition further comprises at least one additional coupler other than said compounds of formula (I).

20. A composition according to claim 1, wherein said composition further comprises at least one direct dye.

21. A composition according to claim 1, wherein said medium suitable for dyeing is chosen from water and a mixture of water and at least one organic solvent.

22. A composition according to claim 21, wherein said at least one organic solvent is chosen from lower $C_1$–$C_4$ alcohols, glycerol, glycols and glycol ethers, and aromatic alcohols.

23. A composition according to claim 19, wherein said at least one additional coupler is chosen from meta-phenylenediamines, meta-aminophenols, meta-diphenols and heterocyclic couplers, and acid-addition salts thereof.

24. A composition according to claim 23, wherein said at least one additional coupler is chosen from indole derivatives and indoline derivatives.

25. A composition according to claim 23, wherein said at least one additional coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole and 6-hydroxyindoline, and acid addition salts thereof.

26. A composition according to claim 19, wherein said at least one additional coupler is present in an amount ranging from 0.0005 to 5% by weight relative to the total weight of said composition.

27. A composition according to claim 24, wherein said at least one additional coupler is present in an amount ranging from 0.005 to 3% by weight relative to the total weight of said composition.

28. A composition according to claim 1, wherein said composition has a pH ranging from 3 to 12.

29. A composition according to claim 28, wherein said composition has a pH ranging from 5 to 11.

30. A composition according to claim 19, wherein said acid addition salts thereof for said at least one coupler are chosen from hydrochlorides, hydrobromides, sulphates, tartrates, lactates, and acetates.

31. A composition according to claim 21, wherein said at least one organic solvent is present in an amount ranging from 1 to 40% by weight relative to the total weight of said composition.

32. A composition according to claim 31, wherein said at least one organic solvent is present in an amount ranging from 5 to 30% by weight relative to the total weight of said composition.

33. A composition according to claim 1, wherein said composition further comprises at least one cosmetically acceptable adjuvant.

34. A composition according to claim 31, wherein said at least one organic solvent is present in an amount ranging from 5 to 30% by weight relative to the total weight of said composition.

* * * * *